(12) United States Patent
Kazerooni et al.

(10) Patent No.: US 10,821,017 B2
(45) Date of Patent: Nov. 3, 2020

(54) TRUNK SUPPORTING EXOSKELETON AND METHOD OF USE

(71) Applicant: The Regents of the University of California, Oakland, CA (US)

(72) Inventors: Homayoon Kazerooni, Berkeley, CA (US); Erich Hacker, Portland, OR (US); Lee-Huang Chen, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 861 days.

(21) Appl. No.: 15/469,201

(22) Filed: Mar. 24, 2017

(65) Prior Publication Data

US 2017/0196712 A1    Jul. 13, 2017

Related U.S. Application Data

(63) Continuation of application No. 14/125,117, filed as application No. PCT/US2012/041891 on Jun. 11, 2012, now Pat. No. 9,655,762.
(Continued)

(51) Int. Cl.
*A61F 5/02* (2006.01)
*A61F 2/70* (2006.01)
(Continued)

(52) U.S. Cl.
CPC ............... *A61F 5/028* (2013.01); *A61F 2/68* (2013.01); *A61F 2/70* (2013.01); *A61F 5/02* (2013.01);
(Continued)

(58) Field of Classification Search
CPC .. A61F 5/00; A61F 5/026; A61F 5/028; A61F 5/68; A61F 5/70; A61F 2007/0024;
(Continued)

(56) References Cited

U.S. PATENT DOCUMENTS 1,202,851 A   10/1916   Kelly
1,409,326 A    3/1922   Williamson
(Continued)

FOREIGN PATENT DOCUMENTS

CN      201934433 U    8/2011
JP       01274758 A   11/1989
(Continued)

OTHER PUBLICATIONS

"U.S. Appl. No. 14/125,117, Examiner Interview dated Jan. 12, 2017", 4 pages.
(Continued)

*Primary Examiner* — Timothy A Stanis
(74) *Attorney, Agent, or Firm* — Kwan & Olynick LLP

(57) ABSTRACT

An exoskeleton includes two torque generators, two thigh links, and a supporting trunk rotatably coupled to the thigh links. When a wearer bends forward in the sagittal plane such that the supporting trunk extends beyond a predetermined angle A with respect to vertical, at least one of the torque generators imposes a resisting torque between the supporting trunk and a corresponding thigh link, thus imposing a force onto a wearer's trunk and thighs to aid in supporting the wearer in a bent position. The exoskeleton may include an active or passive means for actuating the generators. When the supporting trunk does not extend beyond the predetermined angle A, the torque generators do not impose resisting torques between the supporting trunk and the thigh links during the entire range of motion of the thigh links, thus enabling a wearer to walk, run and sit without constraint while in an upright position.

28 Claims, 13 Drawing Sheets

Related U.S. Application Data

(60) Provisional application No. 61/495,484, filed on Jun. 10, 2011.

(51) Int. Cl.
*A61F 2/68* (2006.01)
*A61F 5/01* (2006.01)
*A61F 2/50* (2006.01)

(52) U.S. Cl.
CPC ...... *A61F 5/026* (2013.01); *A61F 2002/5038* (2013.01); *A61F 2002/5039* (2013.01); *A61F 2005/016* (2013.01); *A61F 2005/0169* (2013.01); *A61F 2005/0179* (2013.01); *A61F 2005/0188* (2013.01)

(58) Field of Classification Search
CPC ...... A61F 2007/0027; A61F 2007/0018; A61F 2/68; A61F 2/70; A61H 3/00
See application file for complete search history.

(56) References Cited

U.S. PATENT DOCUMENTS

| | | | |
|---|---|---|---|
| 4,256,098 A | 3/1981 | Swan et al. | |
| 4,745,911 A | 5/1988 | Bender | |
| 4,829,989 A * | 5/1989 | Deamer | A61F 5/02 602/19 |
| 5,176,622 A | 1/1993 | Anderson et al. | |
| 5,207,635 A | 5/1993 | Richards et al. | |
| 5,248,293 A | 9/1993 | Hubbard et al. | |
| 5,259,833 A | 11/1993 | Barnett | |
| 5,275,426 A | 1/1994 | Tankersley | |
| 5,314,404 A | 5/1994 | Boughner et al. | |
| 5,951,591 A * | 9/1999 | Roberts | A61F 5/02 602/36 |
| 6,436,065 B1 | 8/2002 | Mitchell | |
| 7,553,266 B2 | 6/2009 | Abdoli-Eramaki | |
| 7,744,552 B1 * | 6/2010 | Babcock | A61F 5/026 602/19 |
| 7,833,182 B2 * | 11/2010 | Hughes | A61F 5/026 128/845 |
| 8,060,945 B2 | 11/2011 | Adarraga | |
| 8,568,344 B2 | 10/2013 | Ferguson et al. | |
| 9,022,956 B2 | 5/2015 | Kazerooni et al. | |
| 9,655,762 B2 | 5/2017 | Kazerooni et al. | |
| 2005/0130815 A1 * | 6/2005 | Abdoli-Eramaki | A61H 3/008 482/121 |
| 2007/0090143 A1 | 4/2007 | Clayton, III et al. | |
| 2008/0161738 A1 * | 7/2008 | Giesen | A61F 5/026 602/19 |
| 2008/0228121 A1 | 9/2008 | Hughes | |
| 2009/0292369 A1 | 11/2009 | Kazerooni et al. | |
| 2010/0094185 A1 | 4/2010 | Amundson et al. | |
| 2010/0125230 A1 | 5/2010 | Hurley | |
| 2010/0298746 A1 | 11/2010 | Shimizu et al. | |
| 2011/0098617 A1 * | 4/2011 | Ferguson | A61F 5/026 602/16 |
| 2011/0105966 A1 | 5/2011 | Kazerooni et al. | |
| 2011/0111932 A1 | 5/2011 | von Hoffmann et al. | |
| 2011/0266323 A1 | 11/2011 | Kazerooni et al. | |
| 2012/0136292 A1 | 5/2012 | Pepin | |
| 2012/0184881 A1 * | 7/2012 | Kobayashi | A61F 5/026 601/33 |
| 2014/0121573 A1 | 5/2014 | Kazerooni et al. | |
| 2014/0212243 A1 * | 7/2014 | Yagi | A61H 1/024 414/2 |
| 2015/0335461 A1 * | 11/2015 | Kuromiya | B25J 9/0006 248/550 |

FOREIGN PATENT DOCUMENTS

| | | |
|---|---|---|
| JP | 03165765 A | 7/1991 |
| JP | 2007020672 A | 2/2007 |
| JP | 2007097636 A | 4/2007 |
| JP | 2007130234 A | 5/2007 |
| JP | 2007282991 A | 11/2007 |
| JP | 2009011818 A | 1/2009 |
| WO | 2010011848 A1 | 1/2010 |

OTHER PUBLICATIONS

"U.S. Appl. No. 14/125,117, Examiner Interview Summary dated Mar. 23, 2016", 4 pages.
"U.S. Appl. No. 14/125,117, Final Office Action dated Aug. 12, 2016", 19 pages.
"U.S. Appl. No. 14/125,117, Non Final Office Action dated Jan. 11, 2016", 20 pages.
"U.S. Appl. No. 14/125,117, Notice of Allowance dated Feb. 10, 2017", 8 pages.
"U.S. Appl. No. 14/944,635, Examiner Interview Summary dated Mar. 21, 2017", 3 pages.
"U.S. Appl. No. 14/944,635, Examiner Interview Summary dated Apr. 27, 2017", 1 page.
"U.S. Appl. No. 14/944,635, Notice of Allowance dated Apr. 27, 2016", 26 pages.
"Int'l Application Serial No. PCT/US15/61284, ISRWO dated Apr. 11, 2016", 26 pages.

* cited by examiner

TRUNK SUPPORTING EXOSKELETON AND METHOD OF USE

CROSS-REFERENCE TO RELATED APPLICATIONS

This application is a continuation of U.S. application Ser. No. 14/125,117, filed on Dec. 11, 2013, which a 371-national phase entry application of a Patent Cooperation Treaty (PCT) Application No. PCT/US12/41891, filed on Jun. 11, 2012, which claims the benefit of U.S. Provisional Patent Application Ser. No. 61/495,484, filed Jun. 10, 2011. All of the above-referenced patent application are incorporated herein by reference in their entirety.

TECHNICAL FIELD

The present invention pertains to the art of support devices for the human spine, more particularly to a trunk supporting exoskeleton configured to reduce the bending moment on a person's back during a forward bend.

BACKGROUND ART

In general, back support devices which are configured to assist a person in bending, lifting and/or standing upright are known in the art. U.S. Pat. Nos. 6,436,065, 5,951,591, 5,176,622, and 7,744,552. U.S. Pat. Nos. 1,409,326 and 4,829,989 describe devices where moment is created during a bend to counteract the moments from a person's trunk gravity weight. These systems utilize a passive, spring resistance to create a torque between the wearer's torso and legs. By creating a restorative moment at the hip, the probability of injury of the L5/S1 area of the spine is greatly reduced. Once the angle between torso and leg reaches a predetermined angle during stooping, squatting, or walking, the devices provide resistance; however none of the devices differentiate between walking and bending or sitting and bending. This means the user cannot walk comfortably using these passive devices since the user's legs must push against the devices during walking. Similarly the user cannot sit comfortably using these passive devices since the user's legs must push against the devices during sitting. This is uncomfortable and hazardous, preventing the user from moving around unrestricted, and is the most important reason to avoid the use of these systems in various industrial settings. Unlike the aforementioned devices, the technology described here differentiates between walking and bending and between sitting and bending. Even though the relative angle between the user's trunk and a swinging thigh is similar to each other in both cases of bending and walking (or bending and sitting), we have discovered a means by which they can be distinguished using minimal sensing and hardware.

DISCLOSURE OF INVENTION

The present invention is directed to a trunk supporting exoskeleton configured to reduce the muscle forces in a wearer's back during forward lumbar flexion. In general, the exoskeleton includes first and second thigh links configured to couple to a wearer's thighs, and a supporting trunk configured to be coupled to a wearer's trunk. The supporting trunk is rotatably coupled to the thigh links to allow flexion and extension of the thigh links with respect to the supporting trunk. First and second opposing torque generators selectively create torque between the supporting trunk and respective thigh links.

In operation, when a wearer bends forward in the sagittal plane such that a predetermined portion of the supporting trunk deviates or extends beyond a predetermined angle with respect to vertical, at least one of the torque generators imposes a resisting torque between the supporting trunk and a corresponding thigh link. This causes the supporting trunk to impose a force onto a wearer's trunk, and the thigh links to impose forces onto the wearer's respective thighs, thereby helping to support the wearer while in the bent position. In a first embodiment, the exoskeleton includes a passive means for actuating the torque generators. More specifically, when a predetermined portion of the exoskeleton extends past the predetermined angle with respect to vertical, a resilient pendulum comes into contact with an engagement bracket, causing a resisting torque between the supporting trunk and a respective thigh link. In another embodiment, the exoskeleton includes an active means for actuating the torque generators, such as hydraulic motors, pneumatic motors and electric motors.

The exoskeleton may include a signal processor including a controller, which produces a control signal to drive torque generators as a function of a set of input signals received by the signal processor. The input signals may be generated by one or more sensors incorporated into the exoskeleton, such as a velocity sensor, an accelerometer, a force sensor or an angle sensor.

Importantly, when the supporting trunk does not extend beyond the predetermined angle with respect to vertical, the torque generators do not impose resisting torques between the supporting trunk and the thigh links during the entire range of wearer motion of the thigh links. Thus, a wearer is able to walk, run and sit without any constraint while the wearer is in a substantially upright position.

MODES FOR CARRYING OUT THE INVENTION

Figure 1:
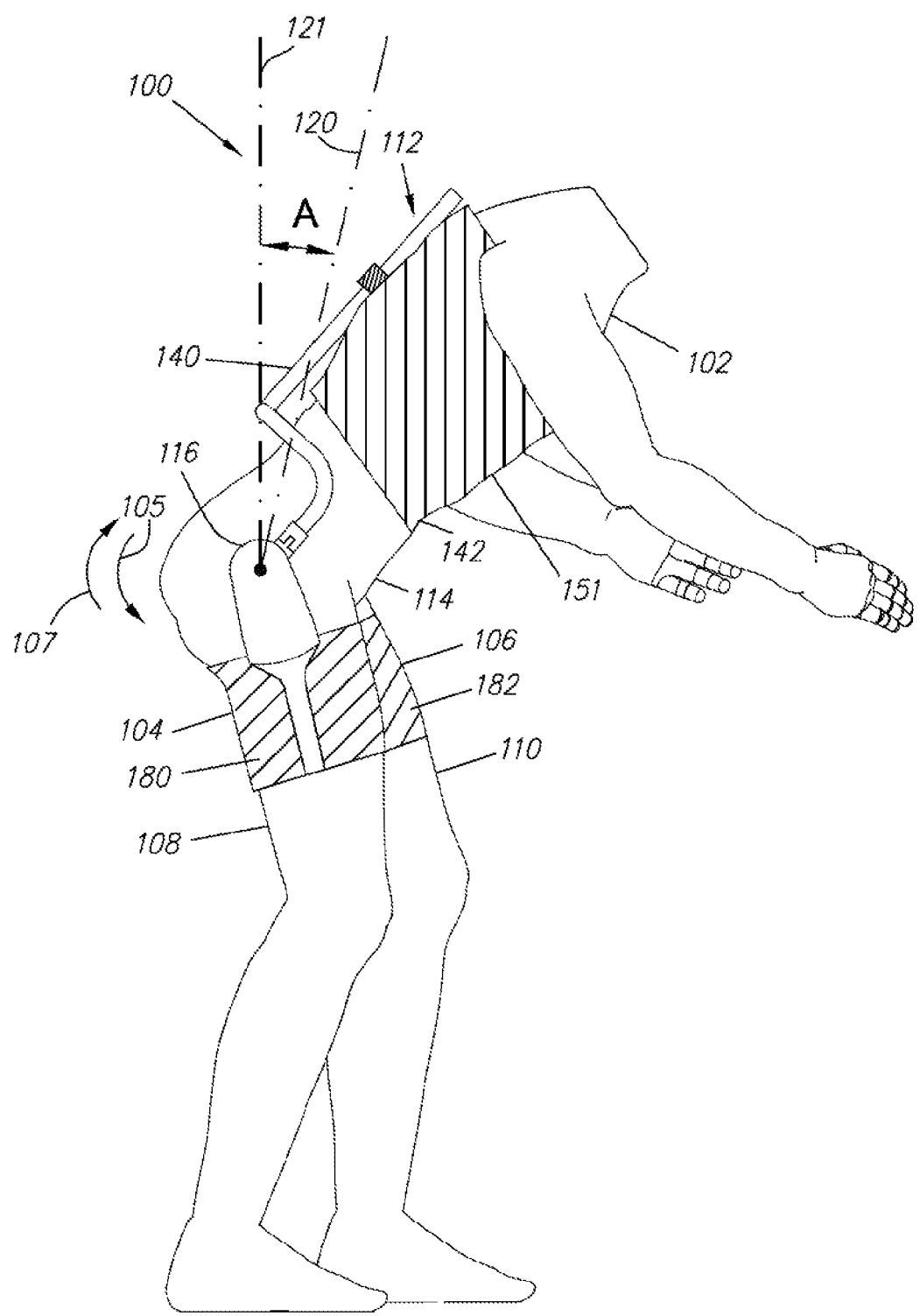
FIG. 1 depicts a trunk supporting exoskeleton of the present invention on a forward leaning wearer.

FIG. 1 illustrates a trunk supporting exoskeleton (referred to as exoskeleton from now on) 100 which is configured to be worn by a person or wearer. Exoskeleton 100, in addition to other functions, reduces the muscle forces in the wearer's back during forward lumbar flexion. In general, exoskeleton 100 comprises: two thigh links 104 and 106 which are configured to couple to a wearer's thighs 108 and 110; and a supporting trunk 112 which is configured to be coupled to the person's trunk 114. Supporting trunk 112 is rotatably coupled to thigh links 104 and 106, allowing for the flexion and extension along arrows 105 and 107 of thigh links 104 and 106 with respect to supporting trunk 112. Additionally, exoskeleton 100 includes first and second opposing torque generators 116 (only one of which is depicted in FIG. 1), capable of creating torques between supporting trunk 112 and respective first and second thigh links 104 and 106.

Figure 2:
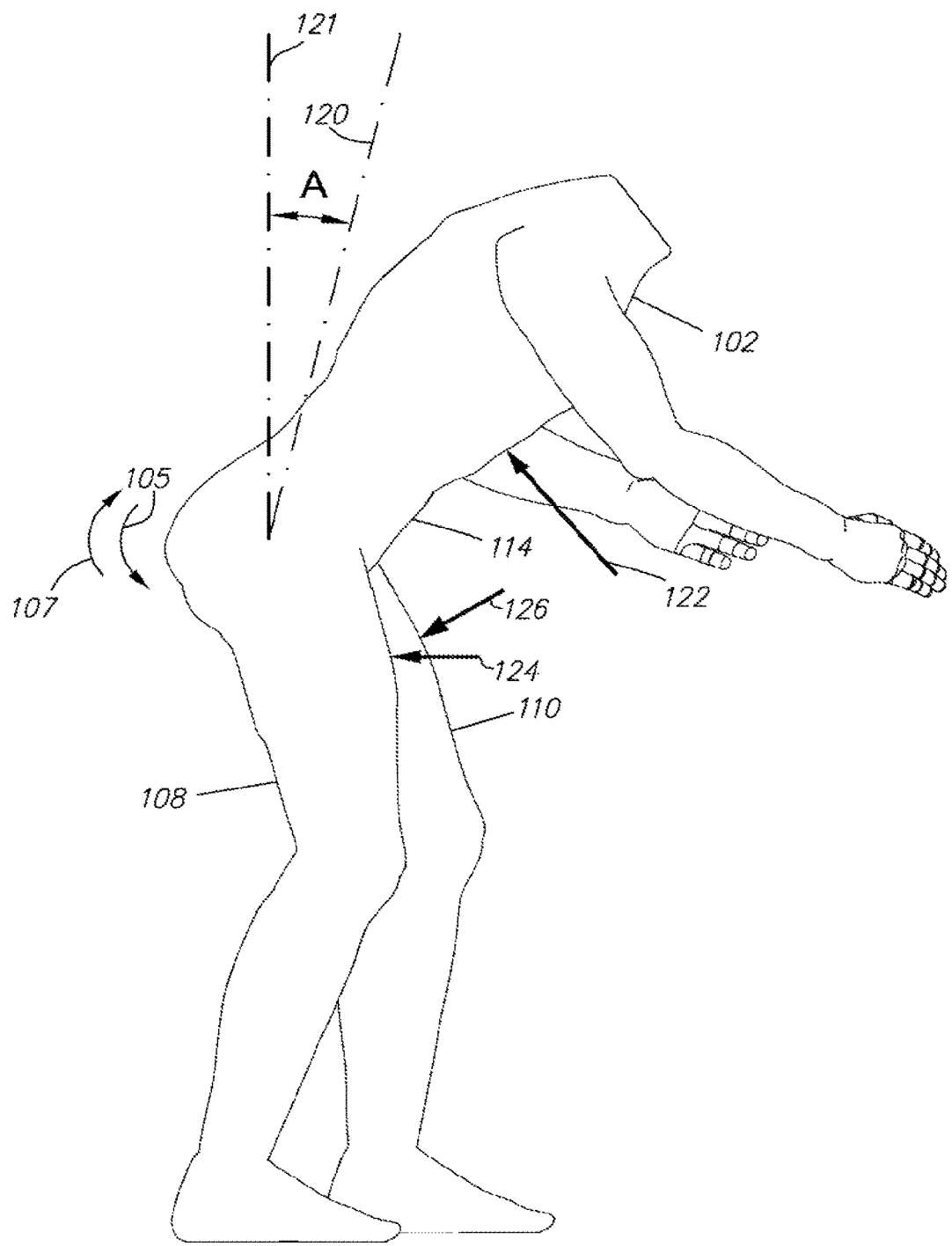
FIG. 2 depicts forces imparted on the wearer of FIG. 1, with the trunk supporting exoskeleton removed for clarity.

In operation, when a wearer bends forward in the sagittal plane such that supporting trunk 112 deviates beyond a straight line 120, at least one of torque generators 116 imposes a resisting torque between supporting trunk 112 and its corresponding thigh link 104, 106. More specifically, line 120 extends at a predetermined angle from a straight vertical line 121, and represents a point beyond which torque generators are actuated. In other words, during forward lumbar flexion, when supporting trunk 112 extends beyond a predetermined angle from vertical, torque is imposed on thigh links 104, 106. As shown in FIG. 2, this device causes supporting trunk 112 to impose a force 122 onto a wearer's trunk 114, and thigh links 104, 106 to impose forces 124 and 126 onto the wearer's respective thighs 108 and 110. It should be understood that exoskeleton 100 can be configured such that torque is imposed on thigh links 104, 106 when a predetermined portion of supporting trunk 112 extends beyond a predetermined angle from vertical. In some embodiment of the invention, torque may be imposed when any portion of trunk 112 extends beyond line 120. In general, exoskeleton 100 can be configured such that torque is imposed on thigh links 104, 106 when supporting trunk 112 shapes itself into a generally bent configuration.

Figure 3:
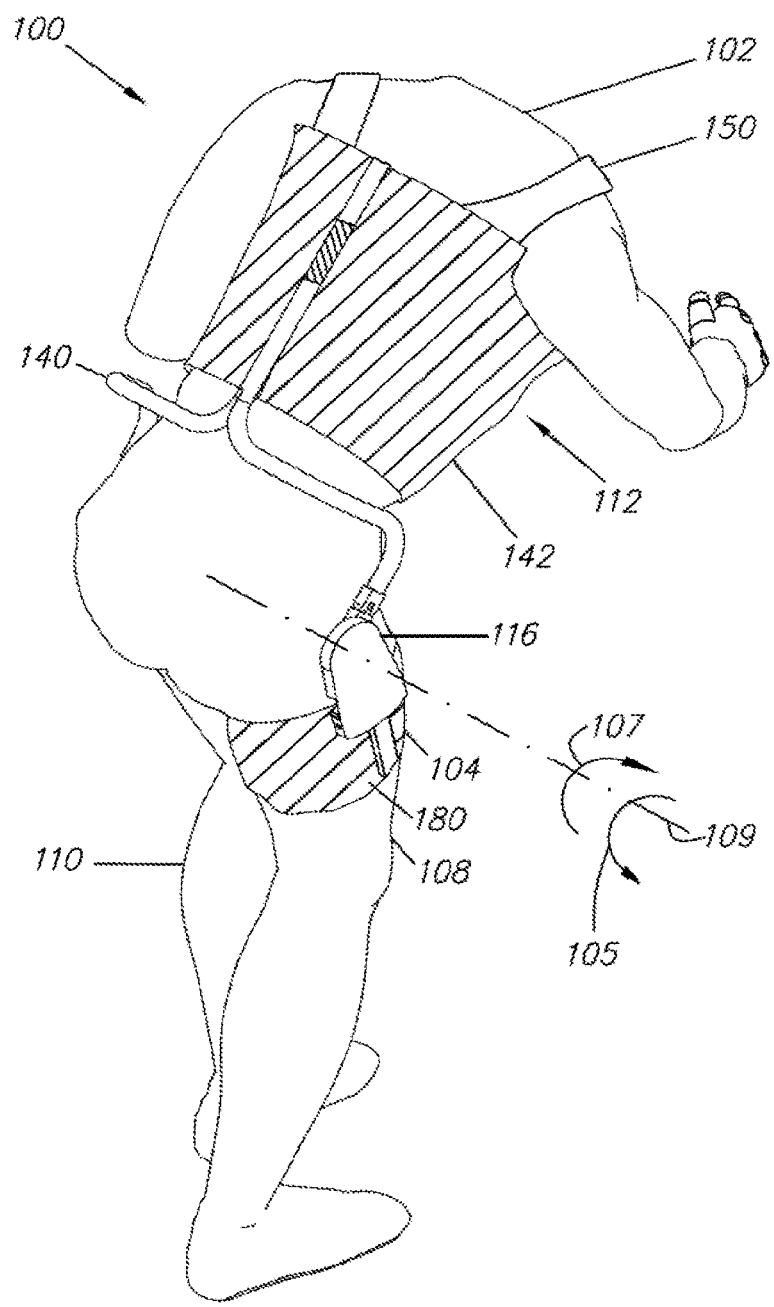
FIG. 3 depicts a back perspective view of a trunk supporting exoskeleton.

Further, in operation, when supporting trunk 112 is not deviated from line 120, torque generators 116 impose no resisting torques between supporting trunk 112 and thigh links 104 and 106 during the entire range of motion of thigh links 104 and 106. This is a unique characteristic of this device where the person can walk, run and sit without any constraint as long as the person's trunk is substantially vertically aligned (i.e. not bent or not deviated beyond line 120). Torque generators 116 have unique characteristics where they only provide resisting torque when the human trunk is bent more than a predetermined value of an angle A, regardless of the human thighs angles with respect to the human trunk 114. As long as the person's trunk does not extend beyond line 120, regardless of the person legs positions and posture, no torque is generated by the torque generators 116. FIG. 3 is a perspective view of the invention where the flexion and extension of thigh link 104 with respect to supporting trunk 112 along axis 109 is depicted clearly.

Figure 4:
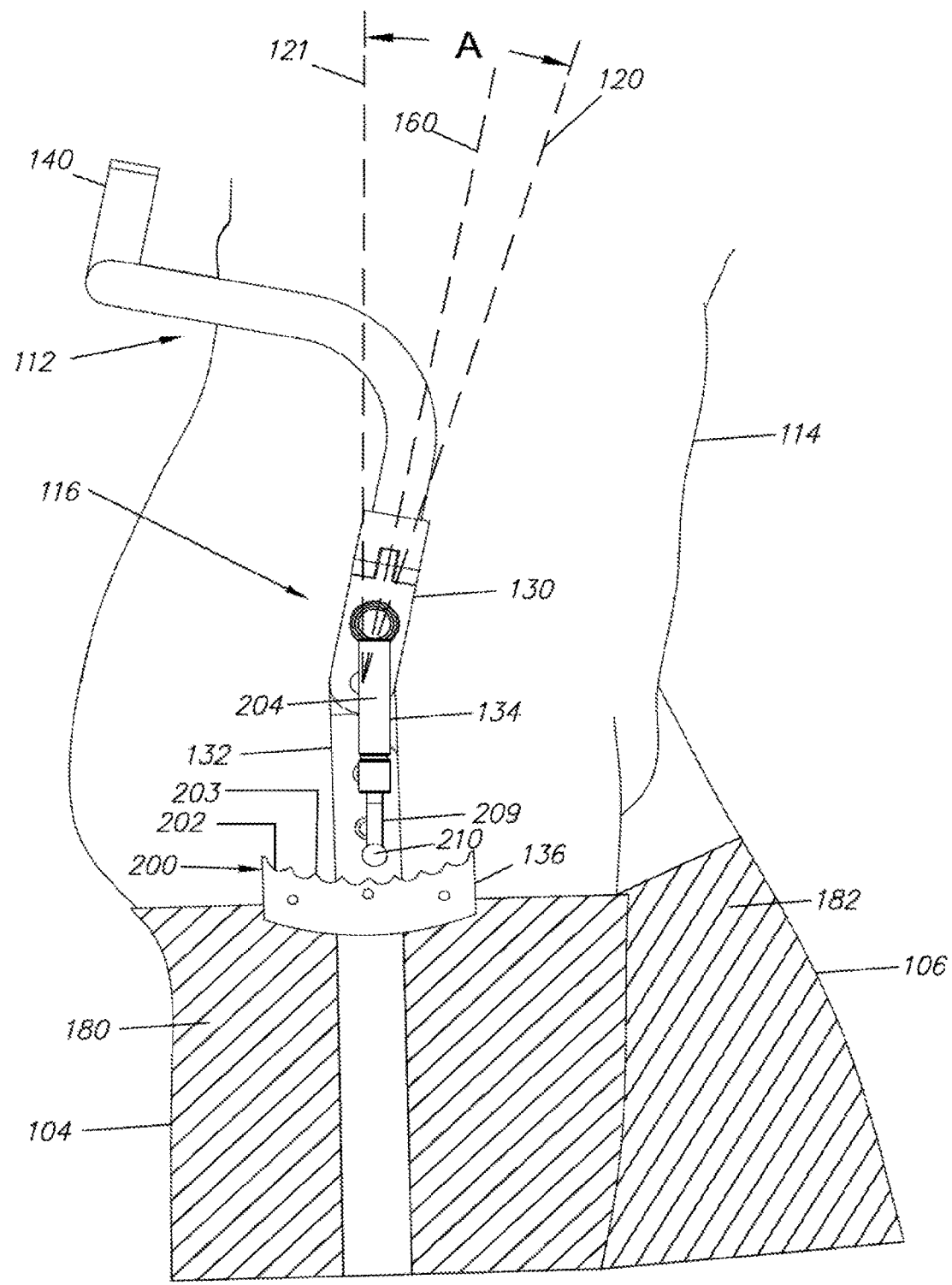
FIG. 4 is a side view of a passive torque generator embodiment of the present invention in an unengaged position.
Figure 5:
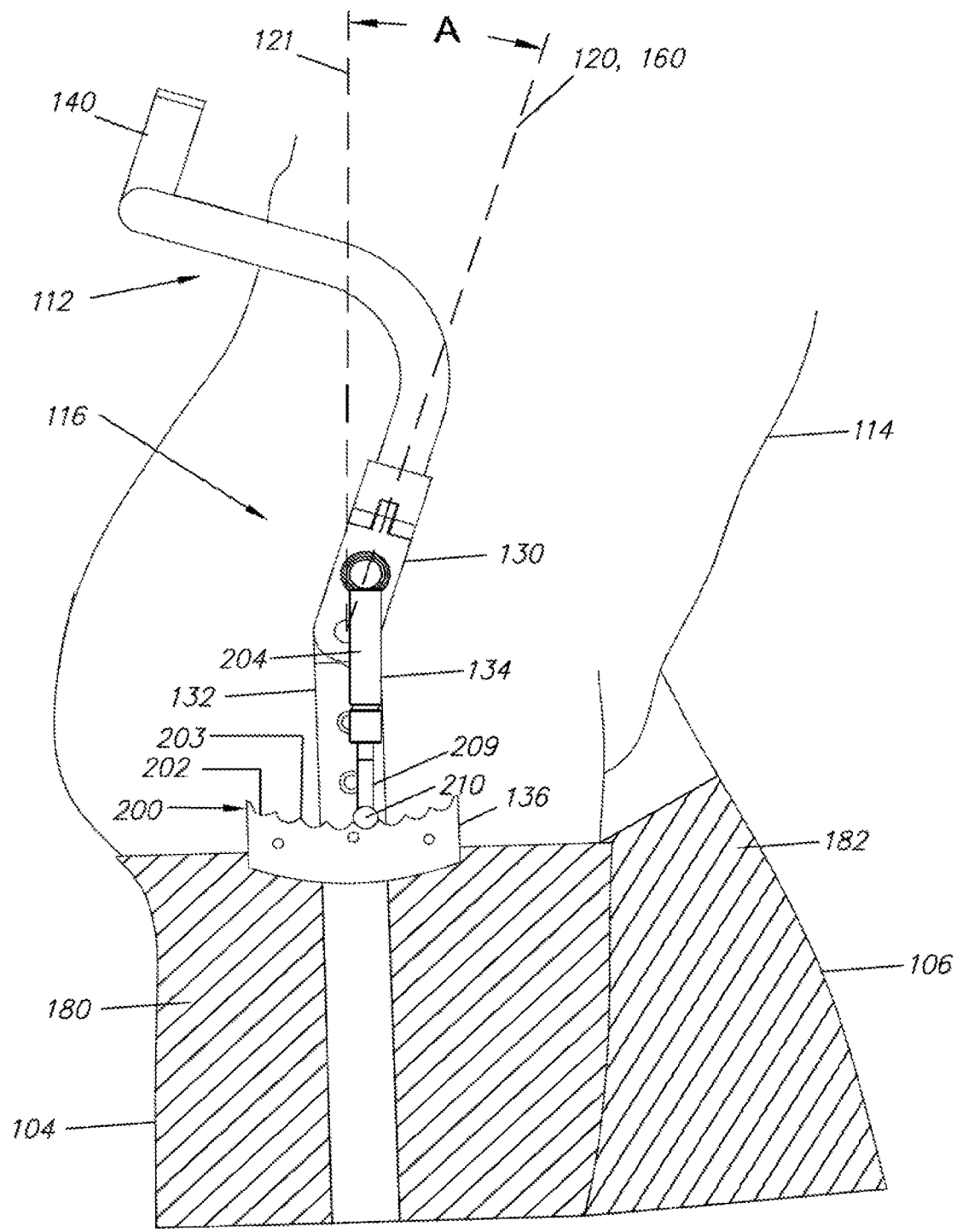
FIG. 5 is a side view of the passive torque generator of FIG. 4 in a first engaged position.

FIG. 4 describes an embodiment of torque generators 116 where respective covers have been removed. It should be noted that torque generators 116 are identical to each other and therefore, only the torque generator shown in FIG. 4 will be discussed in detail. As shown, torque generator 116 comprises: an upper bracket 130 coupled to trunk support 112; a lower bracket 132 coupled to thigh link 104 and rotatably coupled in a sagittal plane to upper bracket 130; a resilient pendulum 134 which is rotatably mounted on upper bracket 130; and an engagement bracket 136 which is securely coupled onto lower bracket 132. In operation, when a predetermined portion of upper bracket 130 extends past line 120, as depicted in FIG. 5, resilient pendulum 134 comes into contact with engagement bracket 136, causing a resisting torque between upper bracket 130 and lower bracket 132. When upper bracket 130 is not deviated from line 120, as depicted in FIG. 4, resilient pendulum 134 will not be in contact with engagement bracket 136, and no resisting torque is produced between upper bracket 130 and lower bracket 132. In some embodiments of the invention resilient pendulum 134 behaves like a compression spring where deflections result in compression forces. In some embodiments of the invention, engagement bracket 136 and lower bracket 132 are a one-piece part.

Figure 6:
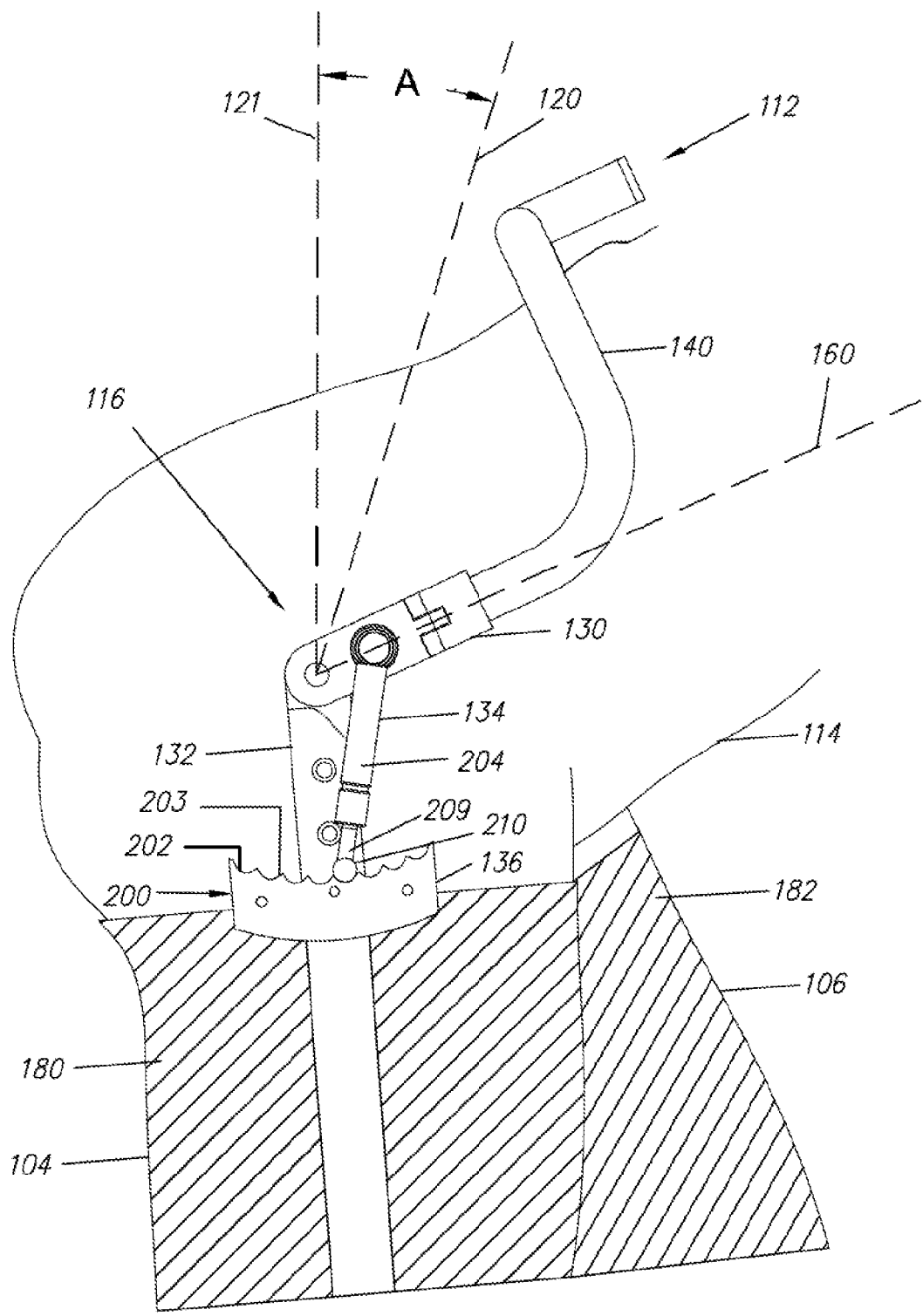
FIG. 6 is a side view of the passive torque generator of FIG. 4 in a second engaged position.

FIG. 6 shows a situation where a person has bent at the waist substantially and resilient pendulum 134 is compressed, such that the length is shortened substantially. In some embodiments of the invention as shown in FIG. 4, FIG. 5 and FIG. 6, resilient pendulum 134 comprises an air spring comprising cylinder 204 and piston 209 moving relative to each other. In some embodiments of the invention, resilient pendulum 134 is a coil spring. Engagement bracket 136 has a profile that does not allow the tip of resilient pendulum 134 to slide relative to bracket 136. In the embodiment of the invention depicted, engagement bracket 136 has a profile that matches the circular profile of the tip of the resilient pendulum 134. More specifically, engagement bracket 136 includes a scalloped upper wall 200 including a plurality of curved divots 202 separated by peaks 203. Resilient pendulum 134 further includes a tip or stop device 210 in the form of a round knob sized to fit within each of curved divots 202. As depicted in FIG. 5, when a wearer bends beyond a predetermined point represented by line 120, stop device 210 engages with one of curved divots 202 and is held in position by peaks 203, such that, upon further bending of the wearer, resilient pendulum 134 will be held in place and the resilient pendulum 134 will compress. In some embodiments of the invention, top upper wall 200 and/or tip 210 may include a frictional surface to prevent the sliding motion of the tip 210 within a curved divot 202.

In some embodiments of the invention, torque generators 116 are active systems. Examples of active torque generators which can be utilized with the present invention include, without limitation, hydraulic motors, pneumatic motors, and electric motors, including, without limitation, alternating current (AC) motors, brush-type direct current (DC) motors, brushless DC motors, electronically commutated motors (ECMs), stepping motors, and combinations thereof. In some embodiments of the invention, torque generators 116 each include an electric motor and a transmission. The resistance supplied by first and second torque generators 116 between supporting trunk 112 and respective thigh links 104 and 106 impose a force onto the person's trunk 114 in the manner depicted in FIG. 1. These torques also cause thigh links 104 and 106 to impose forces onto the person's thighs 108 and 110.

Figure 10:
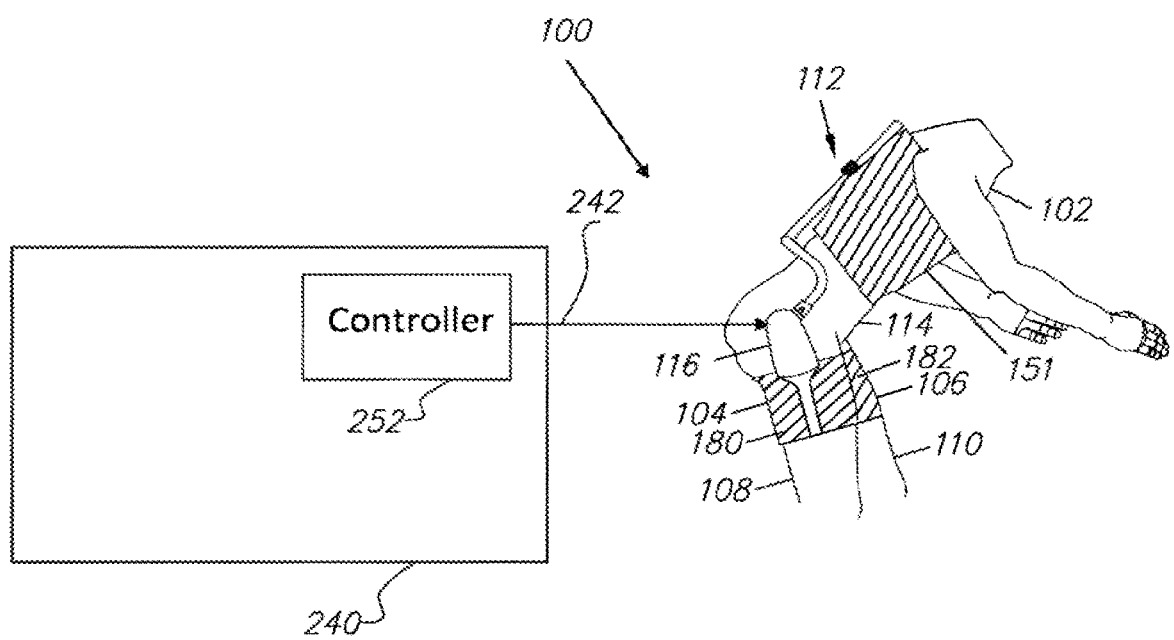
FIG. 10 depicts a signal processor of the present invention.
Figure 11:
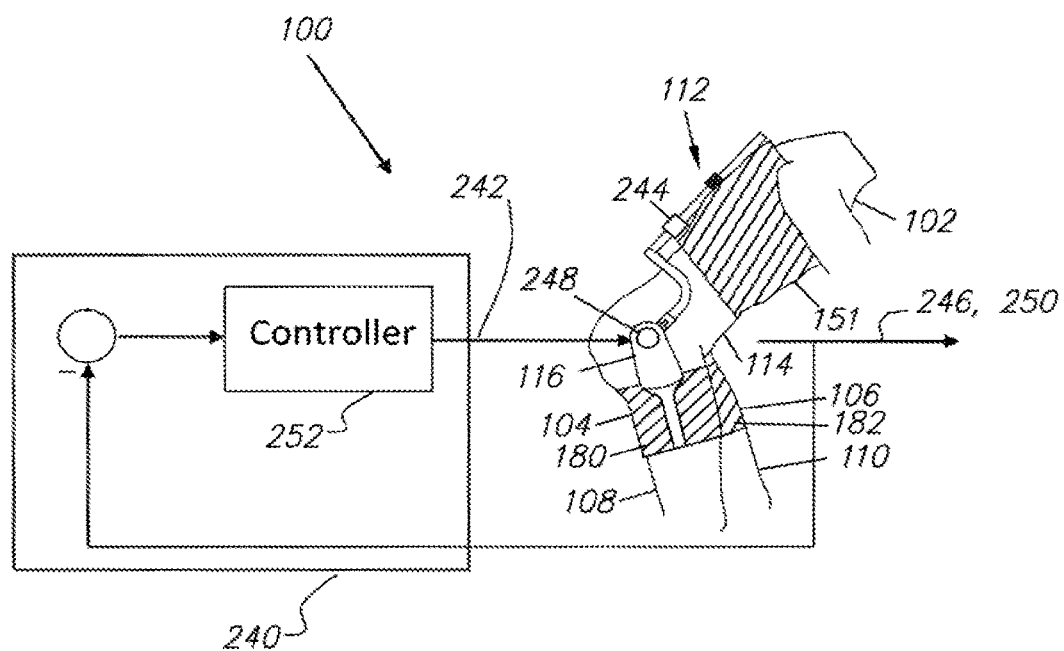
FIG. 11 depicts a first method of control of the present invention.

The manner in which the resistance torque can be automatically adjusted when an active torque generator is used will now be discussed with reference to FIGS. 10-12. In some embodiments of the invention, as shown in FIG. 10, exoskeleton 100 includes a signal processor 240 configured to produce a control signal 242 for torque generators 116, wherein control signal 242 drives torque generators 116. Signal processor 240 incorporates a controller 252 which produces control signal 242 for torque generators 116 as a function of a set of input signals that signal processor 240 receives. Examples of input signals that signal processor 240 receives include, without limitation, signals representing angles of thigh links 104 and 106 with respect to supporting trunk 112, signals representing the velocity of supporting trunk 112 with respect to thigh links 104 and 106, signals representing the acceleration of supporting trunk 112 with respect to thigh links 104 or 106, a signal representing the absolute angle of supporting trunk 112, a signal representing the absolute velocity of supporting trunk 112, a signal representing the absolute acceleration of supporting trunk 112, a signal representing at least one torque generator's movement, a signal representing at least one torque generator's speed, a signal representing at least one torque generator's acceleration, a signal representing at least one torque generator's torque, a signal representing at least one torque generator's force, a signal representing the person's movement, a signal representing the person's bending angle, a signal representing the person's bending velocity, a signal representing the person's bending acceleration, a signal representing the contact force between person 102 and supporting trunk 112, a signal representing an electromyography (EMG) signal from said person and combinations thereof.

Various sensors can be utilized to provide controller 252 with the necessary signal information. In one preferred embodiment depicted in FIG. 11, supporting trunk 112 includes a first sensor 244 generating a first signal 246 representing an output from first sensor 244. In a first example, first sensor 244 is an absolute angle sensor and first signal 246 is an absolute angle signal representing the angle that person 102 or supporting trunk 112 has bent forward relative to line 120 or line 121 (shown in FIG. 1). However, it should be understood that first sensor 244 could be a velocity sensor, an accelerometer or other type of movement sensor. Supporting trunk 112 can also include a second sensor 248 (shown in FIG. 11) generating a second signal 250 representing an output from second sensor 248. In one example, second sensor 248 is an angle sensor and second signal 250 is an angle signal representing the angle of supporting trunk 112 with respect to thigh links 104 or 106. In general, second sensor 248 is either included in the torque generators 116 or installed on the same location on thigh links 104 or 106 or supporting trunk 112 that torque generator 116 are installed. However, it should also be understood that second sensor 248 can be a torque generator movement sensor, a torque generator speed sensor, a torque generator accelerometer, a torque generator torque or force sensor, or any type of standard movement sensor. In operation, as shown in FIG. 11, signal processor 240 produces control signal 242 for torque generators 116 as a function of first signal 246 and/or second signal 250. That is, controller 252 utilizes first and second signals 246 and 250 as a feedback signal to generate control signal 242. The type of controller utilized dictates the magnitude of the resistance torque. One can find a variety of algorithms for controller 252 to perform the indicated task. In general, controllers with large gains lead to large resistance torques, while controllers with small gains result in smaller resistance torque.

Figure 12:
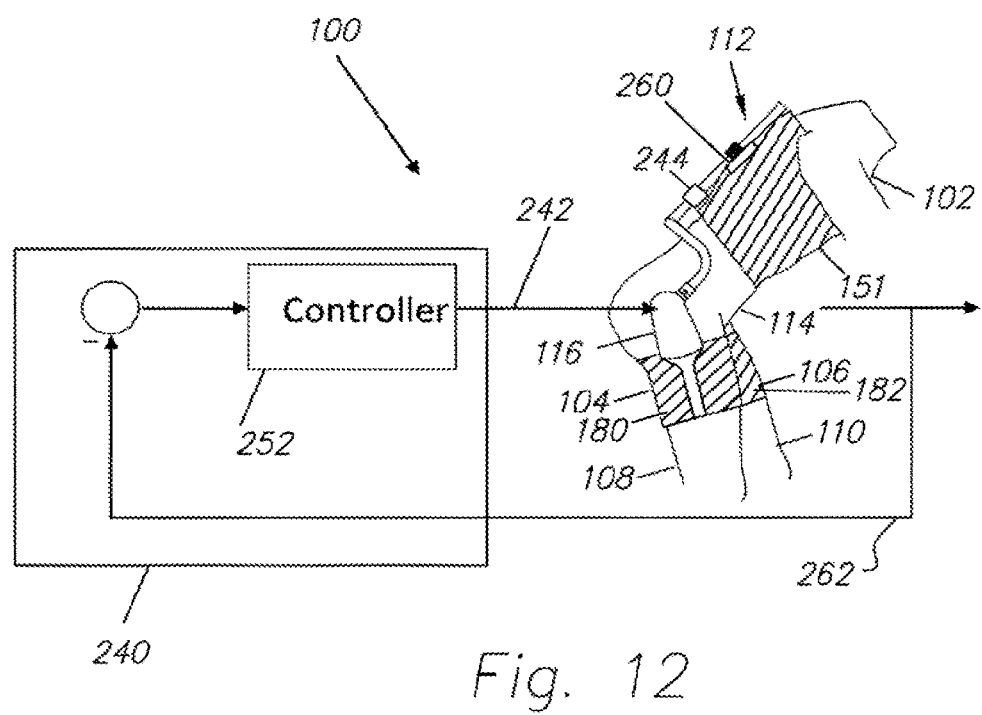
FIG. 12 depicts an alternative method of control of the present invention.

As shown in FIG. 12, exoskeleton 100 may also include a force or pressure sensor 260 generating a force or pressure signal 262 representing the force or pressure between wearer 102 and supporting trunk 112. In operation, signal processor 240 produces control signal 242 for torque generators 116 as a function of force or pressure signal 262. That is, controller 252 utilizes force or pressure signal 262 as a feedback signal to generate control signal 242.

From the discussion above, it should be understood that controller 252 can be programmed and configured to activate torque generators 116 in a variety of ways based on signals 246, 250 and/or 262 from sensors 244, 248 and/or 260. In some embodiments of the invention, the resistance torque is a function of how much person 102 is bending forward. For example, in some embodiments of the invention, the resistance torque increases as person 102 bends forward. In some embodiments of the invention, the resistance torque is a function of the angle between person 102 and a line 120. In some embodiments of the invention, the resistance torque increases linearly as the angle between person 102 and vertical line 121 (shown in FIG. 2) increases. In some embodiments of the invention, the resistance torque is a function of how much supporting trunk 112 moves toward thigh links 104 or 106. In some embodiments of the invention, the resistance torque is a function of the angle between supporting trunk 112 and vertical line 121. In some embodiments of the invention, the resistance torque increases linearly as the angle between supporting trunk 112 and vertical line 121 increases. In some embodiments of the invention, the controller is configured to adjust the resistance torque imposed by the first and second torque generators to be generally constant for at least one segment of a bending movement of a wearer.

In some embodiments of the invention, as shown in FIG. 1 and FIG. 3, supporting trunk 112 comprises a human interface 142, which is configured to be coupled to a person's trunk 114, and a frame 140, which is configured to be coupled to human interface 142. Frame 140 is rotatably coupled to thigh links 104 and 106 allowing for extension and flexion of thigh links 104 and 106 relative to frame 140. Frame 140 comprises any material or combination of materials capable of performing the indicated functions. Examples of materials of frame 140 include, without limitation, aluminum materials, plastic materials, carbon fiber materials, metallic materials, and combinations thereof. In some embodiments of the inventions, frame 140 comprises a plurality of components coupled or hinged to each other.

Figure 7:
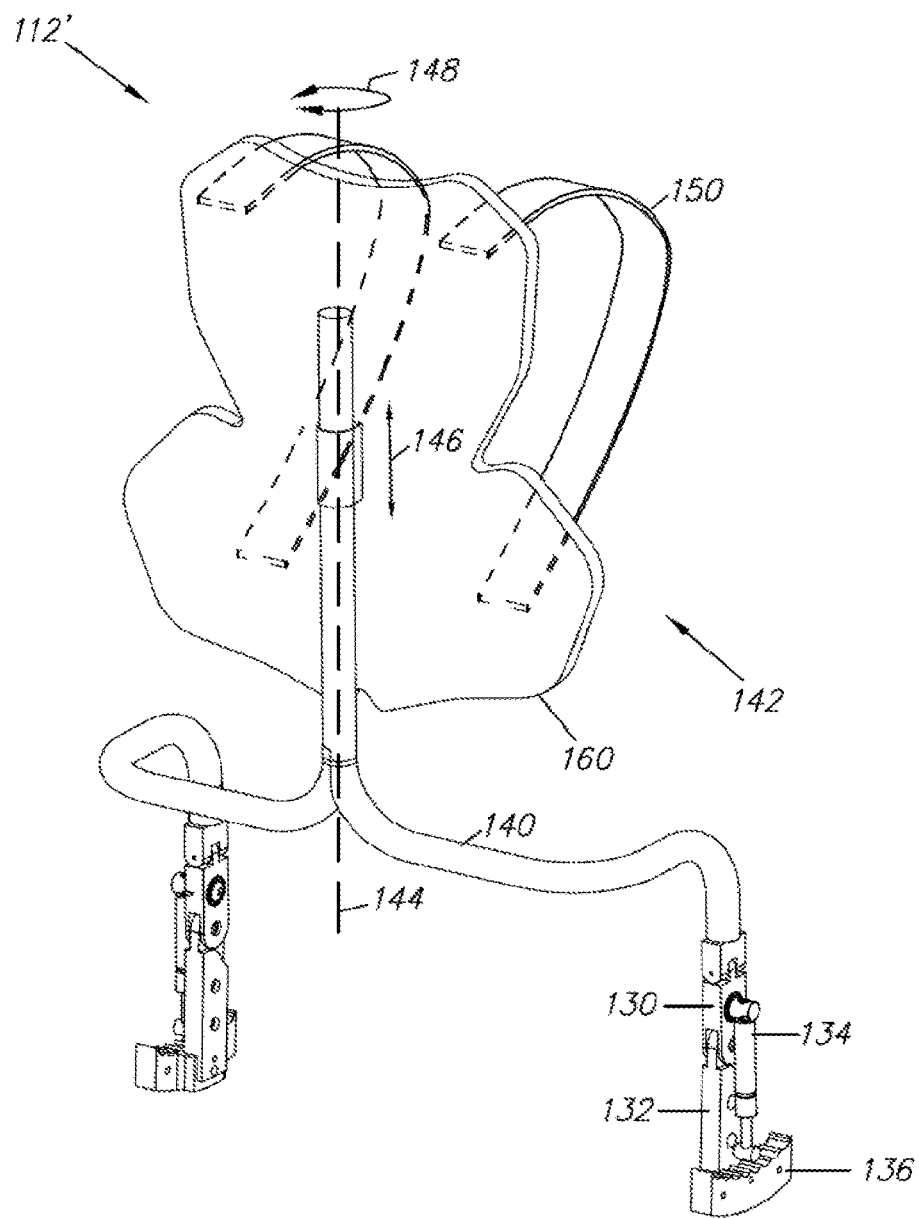
FIG. 7 depicts a human interface embodiment of the supporting trunk.

In some embodiments of the invention, a support trunk 112' includes human interface 142 comprises a back panel 160 to interface the person's back, as depicted in FIG. 7. In some embodiments of the invention, back panel 160 is complaint and deforms as the person bends. In some embodiments of the invention, human interface 142 further comprises at least one shoulder strap 150 configured to couple to the person. Referring back to the embodiment of FIG. 1, the invention may also include a front panel 151 adapted to engage the front of a wearer's trunk 114, to provide additional support. Human interface 142 comprises any material or combination of materials capable of performing the indicated functions. Examples of materials of human interface 142 include, without limitation, fabric materials, plastic materials, belts, leather materials, carbon fiber materials, metallic materials, and combinations thereof.

In some embodiments of the invention, as shown in FIG. 7, human interface 142 is slidable along axis 144 with respect to frame 140 (i.e. slidable along a length of frame 140). This sliding movement, shown by arrow 146, facilitates the bending maneuver of the wearer.

In some embodiments of the invention, as shown in FIG. 7, human interface 142 is rotatable around axis 144 with respect to frame 140. Arrow 148 shows this rotational movement. This rotation allows the person to twist his/her upper body without moving their legs.

Figure 8:
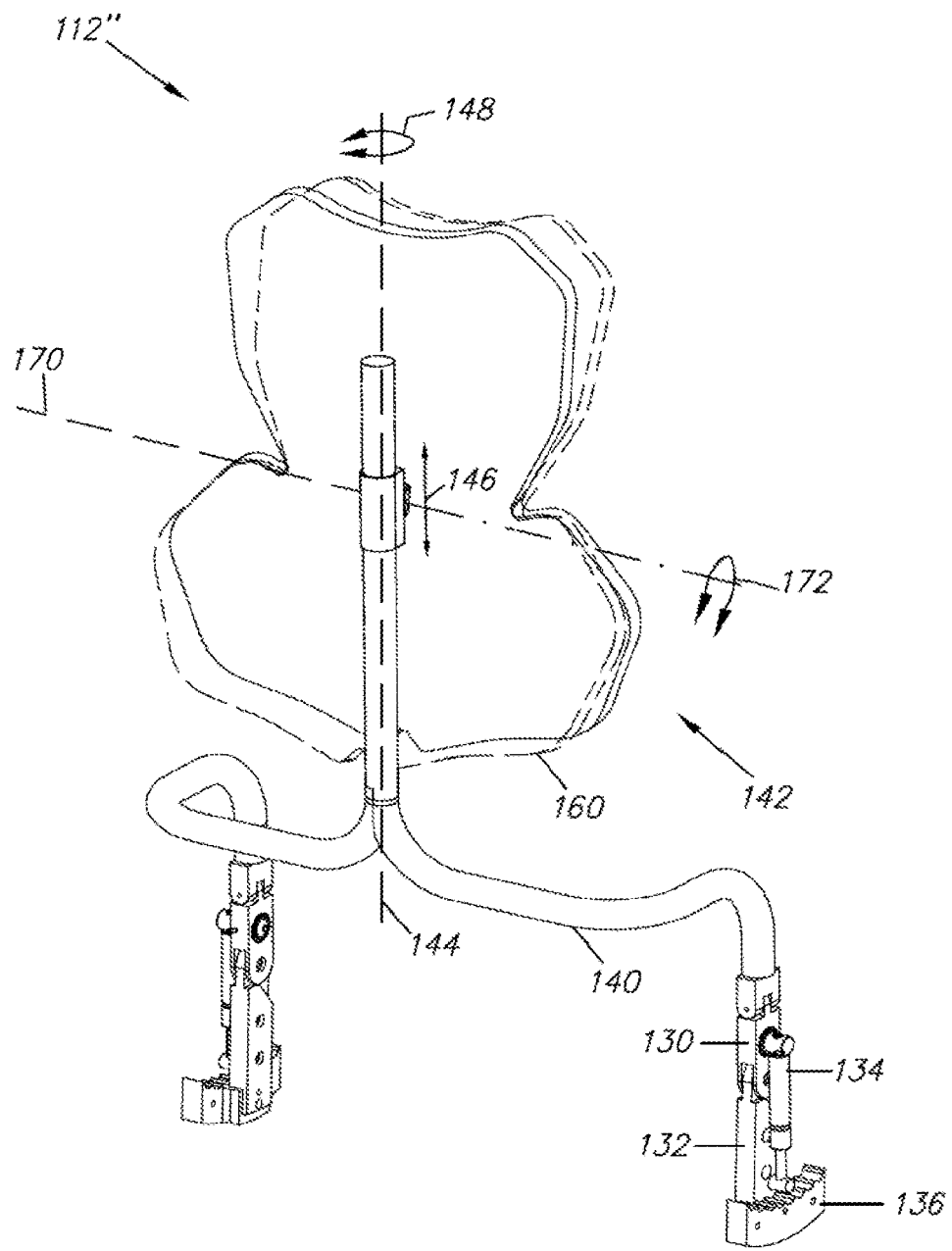
FIG. 8 depicts another human interface embodiment of the supporting trunk.

In some embodiments of the invention, as shown in FIG. 8, a support trunk 112" includes human interface 142 is rotatable around axis 170 with respect to frame 140. Arrow 172 shows this rotational movement. This rotation facilitates the bending maneuver of the person.

Figure 13:
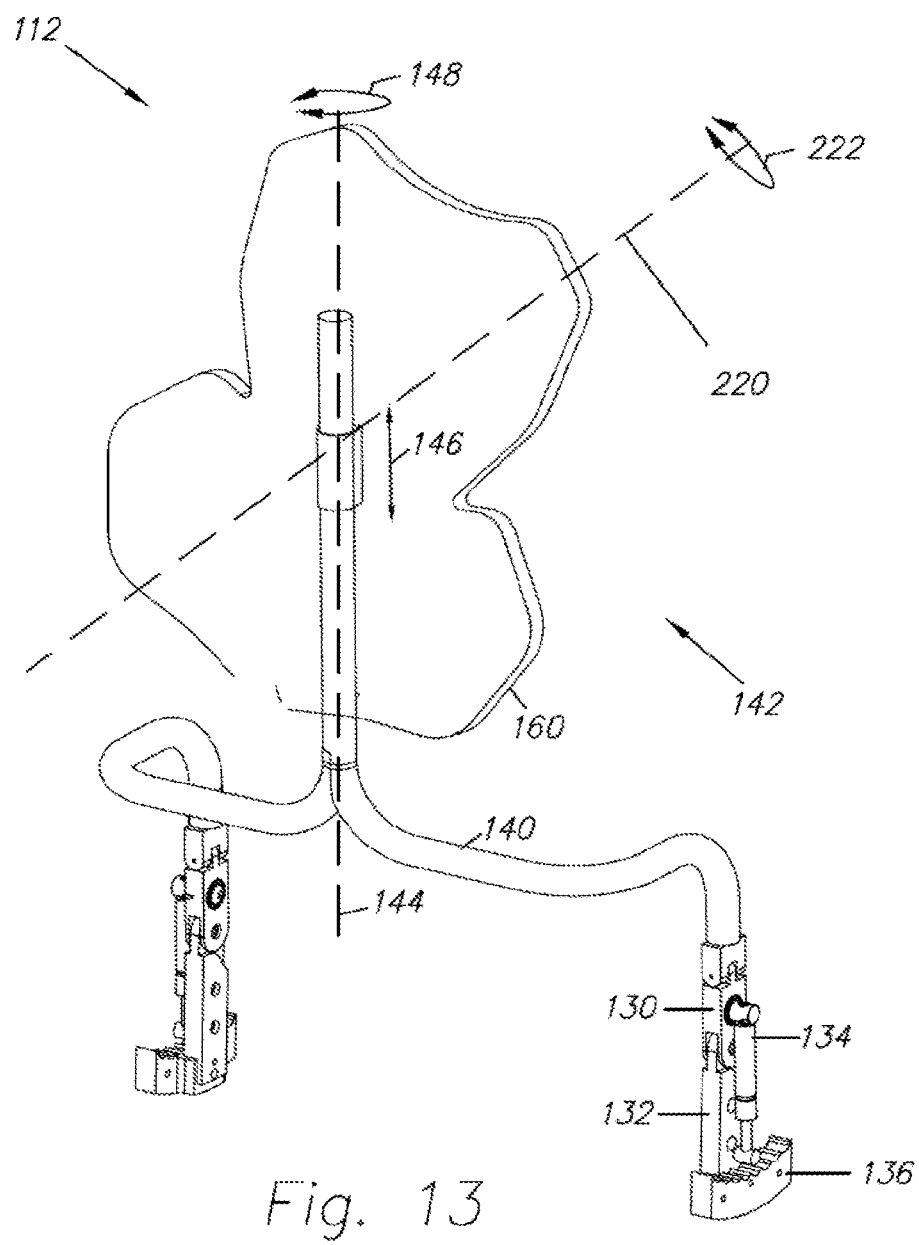
FIG. 13 depicts another human interface embodiment of the supporting trunk.

In some embodiments of the invention, as shown in FIG. 13, human interface 142 is rotatable around axis 220 with respect to frame 140. Arrow 222 shows this rotational movement. This rotation facilitates the rotational maneuver of the person.

In some embodiment of the invention, thigh links 104 and 106 each further comprise at least one thigh strap 180 and 182 configured to couple to person's thighs 108 and 110, as depicted in Figures. Thigh straps 180 and 182 comprise any material or combination of materials capable of performing the indicated functions. Examples of materials of thigh straps 180 and 182 include, without limitation, fabric materials, plastic materials, belts, leather materials, carbon fiber materials, metallic materials, and combinations thereof.

Figure 9:
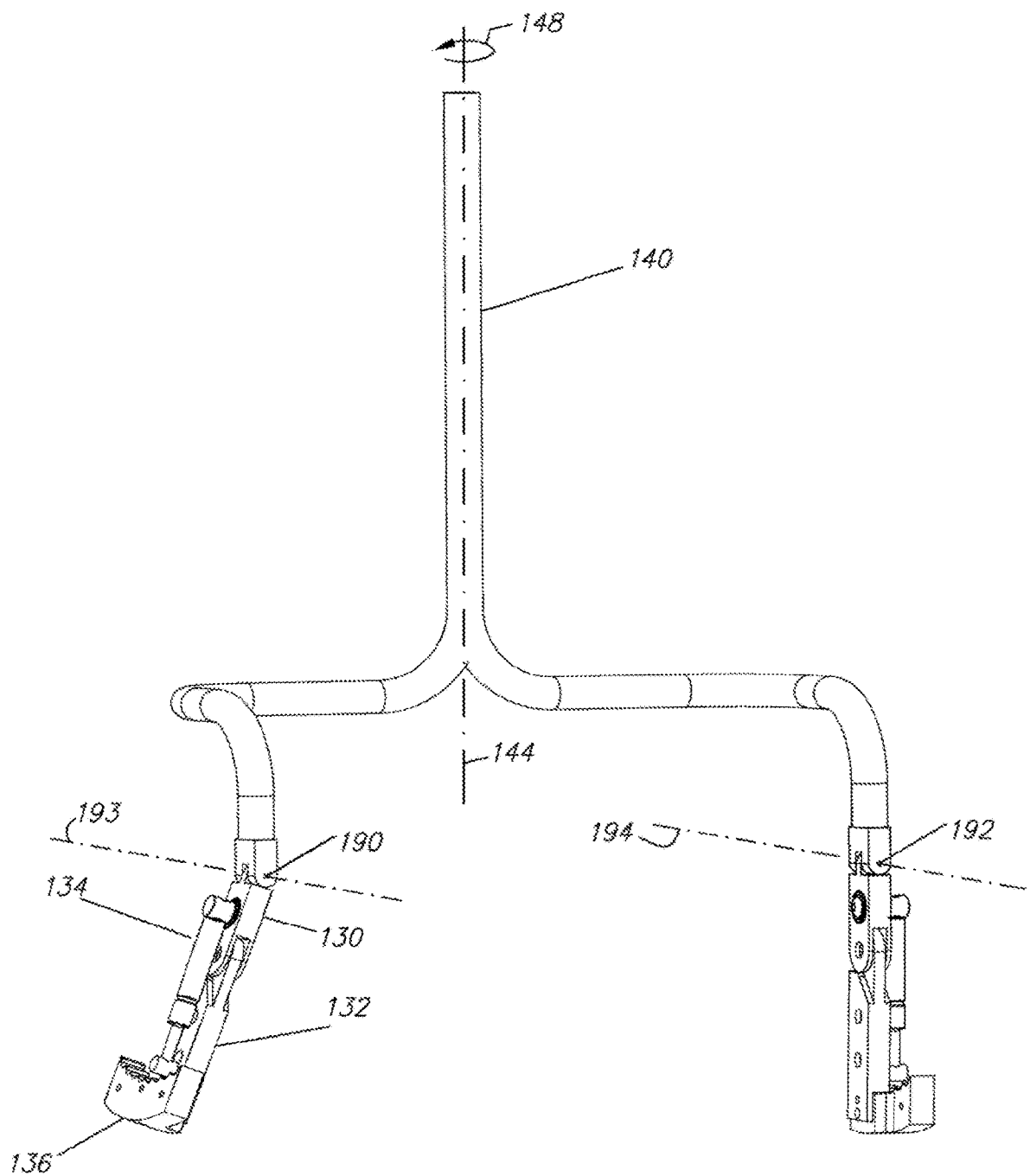
FIG. 9 depicts a portion of the exoskeleton embodiment with abduction and adduction capability.

In some embodiments of invention, as shown in FIG. 9, frame 140 further comprises two rotary abduction-adduction joints 190 and 192 allowing for abduction and adduction of respective thigh links 104 and 106 relative to supporting trunk 112. As shown in FIG. 9, axes 193 and 194 represent the axes of abduction and adduction joints. FIG. 9 shows a portion of supporting trunk 112 where thigh link 104 has abducted.

Although described with reference to preferred embodiments of the invention, it should be readily understood that various changes and/or modifications can be made to the invention without departing from the spirit thereof. For instance, the various human interface, thigh straps and torque generators can be combined in various ways to form different overall embodiments of the present invention. In general, the invention is only intended to be limited by the scope of the following claims.

The invention claimed is:

1. An exoskeleton operable to reduce muscle forces during lumbar flexion of a wearer, the exoskeleton comprising:
   a supporting trunk, operable to be coupled to an upper body of the wearer;
   a first thigh link, operable to be coupled to a first thigh of the wearer and capable of flexion and extension relative to the supporting trunk;
   a second thigh link, operable to be coupled to a second thigh of the wearer and capable of flexion and extension relative to the supporting trunk;
   a first torque generator, operable to generate torque between the first thigh link and the supporting trunk;
   a second torque generator, operable to generate torque between the second thigh link and the supporting trunk;
   at least one sensor, operable to generate at least one input signal; and
   a signal processor operable, to produce at least one control signal derived from the at least one input signal,
      wherein the at least one control signal is operable to control at least one of the first torque generator and the second torque generator such that
         when the at least one input signal indicates that an angle of the supporting trunk from a vertical line becomes larger than a predetermined angle, the signal processor produces a control signal to command at least one of the first torque generator and the second torque generator to generate a resisting torque, thereby causing the supporting trunk to impose a force against the upper body of the wearer.

2. The exoskeleton of claim 1, wherein the at least one input signal is selected from the group consisting of
   a signal representing an angle between the supporting trunk and at least one of the first high link and the second thigh link,
   a signal representing an angular velocity between the supporting trunk and at least one of the first thigh link and the second thigh link,
   a signal representing an angular acceleration between the supporting trunk and at least one of the first thigh link and the second thigh link,
   a signal representing an absolute angle between the supporting trunk and the vertical line,
   a signal representing an absolute angular velocity between the supporting trunk and the vertical line,
   a signal representing an absolute angular acceleration between the supporting trunk and the vertical line,
   a signal representing movement of at least one of the first torque generator and the second torque generator,
   a signal representing a speed of at least one of the first torque generator and the second torque generator,
   a signal representing acceleration of at least one of the first torque generator and the second torque generator,
   a signal representing a torque of at least one of the first torque generator and the second torque generator,
   a signal representing a force of at least one of the first torque generator and the second torque generator,
   a signal representing movement of the wearer,
   a signal representing a bending angle of the wearer,
   a signal representing a bending velocity of the wearer,
   a signal representing a bending acceleration of the wearer, and
   a signal representing a contact force between the wearer and an interface between the supporting trunk and the wearer, and combinations thereof.

3. The exoskeleton of claim 1, wherein the at least one sensor is selected from the group consisting of, a velocity sensor, an accelerometer, a force sensor, a pressure sensor, an angle sensor, a torque generator movement sensor, a torque generator speed sensor, a torque generator force sensor, a torque generator torque sensor, a movement sensor, and a combination thereof.

4. The exoskeleton of claim 1, wherein at least one of the first torque generator and the second torque generator is selected from the group consisting of a hydraulic motor, a pneumatic motor, an electric motor, an alternating current (AC) motor, a brush-type direct current (DC) motor, a brushless DC motor, an electronically commutated motor (ECMs), a stepping motor, and combinations thereof.

5. The exoskeleton of claim 1, wherein at least one of the first torque generator and the second torque generator comprises an electric motor and a transmission.

6. The exoskeleton of claim 1 wherein the signal processor further comprises a controller for generating the at least one control signal as a function of the at least one input signal from the at least one sensor.

7. The exoskeleton of claim 1, wherein the resisting torque is generated as a function of an extent to which the wearer is bending forward.

8. The exoskeleton of claim 1, wherein the resisting torque is generated as a function of an angular distance between the upper body of the wearer and the vertical line.

9. The exoskeleton of claim 1, wherein the resisting torque is generated to increase as an angular distance between the upper body of the wearer and the vertical line increases.

10. The exoskeleton of claim 1, wherein the resisting torque is generated as a function of an extent to which the supporting trunk moves toward at least one of the first thigh link and the second thigh link.

11. The exoskeleton of claim 1, wherein the resisting torque is generated as a function of an angular distance between the supporting trunk and the vertical line.

12. The exoskeleton of claim 1, wherein the signal processor is operable to adjust the resisting torque to be generally constant for at least one portion of a bending movement of the wearer.

13. The exoskeleton of claim 1, wherein the supporting trunk comprises:
a human interface, configured to be coupled to an upper body of the wearer; and
a frame, configured to be coupled to the human interface operable to flex and extend relative to the first link and the second link.

14. The exoskeleton of claim 13, wherein the human interface is moveably connected to the frame such that the human interface can slide along a length of the frame.

15. The exoskeleton of claim 13, wherein the human interface is rotatable with respect to the frame.

16. The exoskeleton of claim 13, wherein the human interface comprises at least one shoulder strap configured to be coupled to the wearer.

17. The exoskeleton of claim 13, wherein the human interface comprises a back panel configured to interface with a back of the wearer.

18. The exoskeleton of claim 13, wherein the frame further comprises first and second rotary abduction-adduction joints enabling abduction and adduction of the respective first and second thigh links relative to the supporting trunk.

19. The exoskeleton of claim 13, wherein the human interface comprises a front panel, configured to interface a front of the wearer.

20. The exoskeleton of claim 19, wherein the human interface is made from a material or combination of materials selected from the group consisting of fabric, plastic, leather, carbon fiber, metal, and combinations thereof.

21. The exoskeleton of claim 1, wherein each of the first link and the second link comprises at least one strap, configured to couple each of the first link and the second link to the wearer.

22. The exoskeleton of claim 21, wherein the at least one strap is made from a material or a combination of materials selected from the group consisting of fabric, plastic, leather, carbon fiber, metal, and combinations thereof.

23. The exoskeleton of claim 1, wherein the resistance torque imposed by at least one of the first torque generator and the second torque generator is a function of how much the supporting trunk bends.

24. The exoskeleton of claim 1, wherein the resistance torque imposed by at least one of the first torque generator and the second torque generator increases automatically as the supporting trunk bends.

25. The exoskeleton of claim 1, wherein the resistance torque increases linearly as the angle between the supporting trunk and the vertical line increases.

26. An exoskeleton, operable to be worn by a wearer to reduce muscle forces during forward spinal flexion, the exoskeleton comprising:
a supporting trunk, operable to couple to an upper body of the wearer;
at least one link, coupled to the supporting trunk and operable to move in unison with a body member of the wearer,
wherein the at least one link is capable of flexion and extension relative to the supporting trunk; and
at least one active torque generator, operable to allow free movement of the at least one link relative to the supporting trunk when the spine of the wearer has not flexed beyond a predetermined angle,
wherein the at least one active torque generator automatically starts to generate resisting torque between the at least one link and the supporting trunk when the spine of the wearer flexes beyond a predetermined angle from a vertical line.

27. An exoskeleton, operable to be worn by a wearer to reduce muscle forces during forward spinal flexion, the exoskeleton comprising:
a supporting trunk, operable to be coupled to an upper body of the wearer;
at least one link, coupled to the supporting trunk and operable to move in unison with a body member of the wearer,
wherein the at least one link is capable of flexion and extension relative to the supporting trunk; and
at least one active torque generator, operable to allow for free movement of the at least one link relative to the supporting trunk when a predetermined portion of the supporting trunk has not extended beyond a predetermined angle from a vertical line,
wherein the at least one active torque generator automatically starts to generate a resisting torque, thereby imposing a supporting force on the wearer when the predetermined portion of the supporting trunk extends beyond the predetermined angle from the vertical line.

28. The exoskeleton of claim 1, wherein the resisting torque increases linearly as an absolute angle between the supporting trunk and the vertical line increases.

* * * * *